US010241044B2

(12) United States Patent
Wong et al.

(10) Patent No.: US 10,241,044 B2
(45) Date of Patent: Mar. 26, 2019

(54) NDIR GLUCOSE DETECTION IN LIQUIDS

(71) Applicant: Airware, Inc., Goleta, CA (US)

(72) Inventors: Jacob Y Wong, Goleta, CA (US); Thomas Campbell, Newbury Park, CA (US)

(73) Assignee: AIRWARE, INC., Goleta, CA (US)

( * ) Notice: Subject to any disclaimer, the term of this patent is extended or adjusted under 35 U.S.C. 154(b) by 0 days.

(21) Appl. No.: 16/056,531

(22) Filed: Aug. 7, 2018

(65) Prior Publication Data

US 2019/0025207 A1    Jan. 24, 2019

Related U.S. Application Data

(63) Continuation of application No. 15/785,829, filed on Oct. 17, 2017, now Pat. No. 10,041,881, and a continuation-in-part of application No. 15/644,775, filed on Jul. 8, 2017, now Pat. No. 9,823,185, said application No. 15/785,829 is a continuation-in-part
(Continued)

(51) Int. Cl.
| | |
|---|---|
| *G01N 21/59* | (2006.01) |
| *G01N 33/49* | (2006.01) |
| *G01N 21/35* | (2014.01) |
| *G01N 21/27* | (2006.01) |
| *G01J 3/42* | (2006.01) |
| *G01N 21/3577* | (2014.01) |
| *G01J 3/427* | (2006.01) |

(Continued)

(52) U.S. Cl.
CPC ............. *G01N 21/59* (2013.01); *G01J 3/427* (2013.01); *G01N 21/274* (2013.01); *G01N 21/3577* (2013.01); *G01N 33/49* (2013.01); *G01N 2021/3148* (2013.01); *G01N 2021/473* (2013.01); *G01N 2201/0696* (2013.01); *G01N 2201/127* (2013.01)

(58) Field of Classification Search
CPC ... G01J 3/427; G01N 21/274; G01N 21/3577; G01N 21/59; G01N 33/49; G01N 2021/3148; G01N 2021/473; G01N 2201/0696; G01N 2201/127
See application file for complete search history.

(56) References Cited

U.S. PATENT DOCUMENTS

| | | | |
|---|---|---|---|
| 6,509,567 B2 * | 1/2003 | Boudet | G01M 3/002 250/343 |
| 2005/0012042 A1 * | 1/2005 | Weckstrom | G01N 21/3504 250/343 |

(Continued)

*Primary Examiner* — Mark R Gaworecki
(74) *Attorney, Agent, or Firm* — Roy L. Anderson

(57) ABSTRACT

For determining concentration of targeted molecules $M_G$ in a liquid sample admixed with interfering molecules $M_J$ which overlap their absorption band, a special NDIR sampling and calibration technique is employed. Besides the signal source, a reference and one or more interference sources are added. The selection of the wavelength for the interference sources enables its measured transmittance value to be used for deciding the validity of the calibration curve for molecules $M_G$ in the liquid sample. This value can further be used to adjust the calibration curve via a parameter linking the transmittances measured at the signal and interference wavelength channels in order to assure its validity.

10 Claims, 4 Drawing Sheets

Related U.S. Application Data of application No. 15/644,775, which is a continuation-in-part of application No. 15/594,418, filed on May 12, 2017, now Pat. No. 9,726,601, which is a continuation-in-part of application No. 15/444,136, filed on Feb. 17, 2017, now Pat. No. 9,678,000, which is a continuation-in-part of application No. 15/358,873, filed on Nov. 22, 2016, now Pat. No. 9,606,053.

(51) Int. Cl.
    *G01N 21/47* (2006.01)
    *G01N 21/31* (2006.01)

(56) References Cited

U.S. PATENT DOCUMENTS

| | | | |
|---|---|---|---|
| 2012/0097852 A1* | 4/2012 | Weckstrom | G01N 21/314 250/343 |
| 2017/0265787 A1 | 9/2017 | Wong | |

* cited by examiner

NDIR GLUCOSE DETECTION IN LIQUIDS

CROSS-REFERENCE TO RELATED APPLICATIONS

The present invention is a continuation-in-part application of U.S. Ser. No. 15/785,829 filed Oct. 17, 2017, which is a continuation-in-part of U.S. Ser. No. 15/644,775 filed Jul. 8, 2017, which was issued on Nov. 21, 2017 as U.S. Pat. No. 9,823,185, which is a continuation in part of U.S. Ser. No. 15/594,418 filed May 12, 2017, which was issued on Aug. 8, 2017 as U.S. Pat. No. 9,726,601, which is a continuation-in-part application of U.S. Ser. No. 15/444,136 filed Feb. 27, 2017, which was issued on Jun. 13, 2017 as U.S. Pat. No. 9,678,000, which is a continuation-in-part application of U.S. Ser. No. 15/358,873, filed Nov. 22, 2016, which was issued on Mar. 28, 2017 as U.S. Pat. No. 9,606,053, the disclosures of all of which are specifically incorporated herein by reference.

FIELD OF THE INVENTION

The present invention relates to a new Non-Dispersive Infra-Red (NDIR) measurement technique capable of significantly reducing scattering noise for detecting molecules in liquids.

BACKGROUND OF THE INVENTION

Non-Dispersive Infra-Red (NDIR) is a common and excellent measurement technique for detecting gases in the atmosphere. NDIR sensors utilize the principle that various gas molecules exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating. The optical filter isolates the radiation in a particular wavelength band that coincides with a strong absorption band of a gas species for the purpose of said gas species measurement.

For detecting molecules in liquids, the NDIR measurement method, which works well in the gaseous phase where the molecular density is low, encounters debilitating measurement noise caused by scattering because of the much higher molecular density in liquids. As disclosed by Wong and Campbell in U.S. Pat. No. 9,606,053 (2017), a method is advanced which significantly suppresses the noise attributable to scattering in the liquids. For determining the concentration of targeted molecules labeled M in a liquid sample admixed with interfering molecules labeled $M_J$ which overlap the absorption band of molecules M, a unique sampling methodology for reducing the interference noise uses an additional interference radiation source besides those of the signal and reference is further advanced by Wong and Campbell in U.S. Pat. No. 9,606,053 (2017). The present invention is to extend the use of this unique sampling methodology to quantify the extent of the inaccuracy caused by the interfering molecules and to rectify the calibration curve for ensuring its future applicable validity.

SUMMARY OF THE INVENTION

The present invention is generally directed to a process for determining a concentration of a targeted molecule M within a given time period in a liquid sampling matrix in which at least one interfering molecule $M_J$ coexists with the targeted molecule by use of a non-invasive apparatus. Infrared radiation is pulsed from a signal source, an interference source and a reference source into a multiplexer and radiation leaving the multiplexer is collimated into a pulsed beam which is directed at a spot of a liquid sampling matrix. Infrared radiation is detected by a detector after it emerges from the spot as a pulsed signal and reference channel output and a pulsed interference signal and reference channel output from the pulsed beam after it penetrates into the spot. Signal processing is used to obtain an average ratio value of $R_{ave}(t)$ for a first preselected period of time ("t") from the pulsed signal and reference channel output, where $R_{ave}(t)$=signal channel/reference channel output for the first preselected period of time. Signal processing is used to obtain an average ratio value of $R_{Jave}(t_2)$ for a second preselected period of time ("$t_2$") from the pulsed interference and reference channel output, where $R_{Jave}(t_2)$=interference channel/reference channel output for the second preselected period of time. A chosen calibration curve is determined for the non-invasive apparatus and then electronics are used to calculate the concentration of the targeted molecule M in the liquid sampling matrix by use of $R_{ave}(t)$ and the chosen calibration curve. The concentration of the targeted molecule M in the liquid sampling matrix is provided as an output from electronics. The signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band. At least one interfering molecule $M_J$ absorbs radiation at the signal wavelength. The signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency. The chosen calibration curve is obtained by the steps of: (1) using the non-invasive apparatus to obtain a set of calibration curves for a set of different known concentration samples wherein each of the set of calibration curves contains a plurality of assumed β values, wherein β is a parameter indicating the ratio of the absorption strength of interfering molecules measured respectively at the signal wavelength and the interference wavelength; (2) using the non-invasive apparatus to calculate the concentration of the targeted molecule M in a known concentration calibration sample by use of $R_{ave}(t)$ and determining a best calibration curve of the set of calibration curves which achieves a calculated concentration closest to a known concentration of the known calibration sample; and (3) using the best calibration curve as the chosen calibration curve.

Accordingly, it is an object of the present invention to provide a new Non-Dispersive Infra-Red (NDIR) measurement technique capable of significantly reducing scattering noise for detecting molecules in liquids.

This and further objects and advantages will be apparent to those skilled in the art in connection with the figures and the detailed description of the invention set forth below.

DETAILED DESCRIPTION OF THE INVENTION

Figure 1:
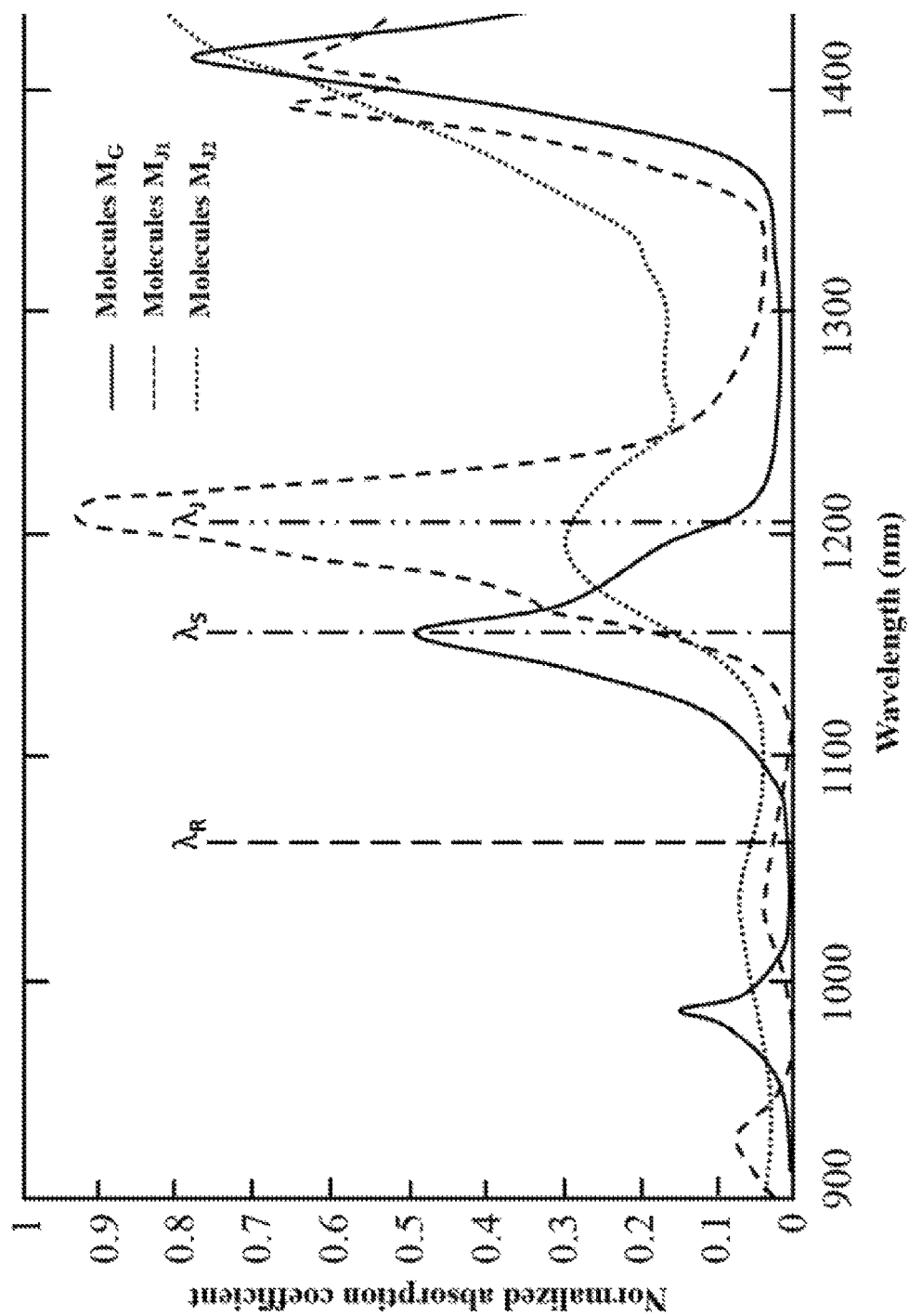
FIG. 1 shows the normalized absorption coefficients for targeted molecules M and interference molecules $M_J$ ($M_{J1}$ and $M_{J2}$) as a function of wavelength.

As disclosed by Wong and Campbell in U.S. Pat. No. 9,606,053 (2017), an NDIR method is advanced which significantly suppresses the scattering noise attributable to the much higher molecular density encountered in liquids. The method utilizes alternating and successively pulsing infrared radiation from signal and reference sources which are multiplexed and collimated into a single pulsed beam directed through the liquid sample. The pulse frequency is set sufficiently fast so as to provide almost the same molecular configuration to both the signal and the reference beams. The scattering noise encountered by both beams is effectively the same and can be significantly reduced through processing the ratio of their respective pass-through outputs.

For determining the concentration of targeted molecules labeled M in a liquid sample admixed with interfering molecules labeled $M_J$, a method was advanced by Wong and Campbell in U.S. Pat. No. 9,726,601 (2017) which uses an additional interference radiation source besides those of the signal and reference to significantly reduce the interference noise. The present invention is to extend the use of this unique sampling methodology to quantify the extent of the inaccuracy caused by the interfering molecules and to use it to validate and rectify if necessary the concentration calibration curve of the targeted molecules M in order to ensure target species measurement accuracy.

An NDIR sensor used to detect molecules in a liquid typically utilizes an infrared source which sends radiation through a chamber containing the sample to a detector which has a spectral filter that passes only radiation which coincides with the absorption band of the molecules to be detected. An alternate way to carry out the operation is for the source, such as a laser, to define and limit the spectral radiation incident at the detector after passing through the liquid sample. In either case the Physics is governed by the Beer-Lambert law which states that the transmission of light at a particular wavelength $\lambda$ through a medium such as a liquid sample is expressed as:

$$I = I_0 \exp(-OD); T = I/I_0 \text{ and } A = 1 - T \quad (1)$$

where $I_0$ is the initial light intensity, I is the intensity after passing the sample medium, T is the transmittance, A is the absorption and OD is the Optical Depth which is a function of the concentration of molecules in the liquid sample to be detected and the sample path length. The concentration level of a particular kind of molecule in a liquid having an absorption band wavelength $\lambda_S$ can be determined by measuring the transmittance $T(\lambda_S) = 1 - A(\lambda_S)$ with radiation having wavelength $\lambda_S$. In other words, a calibration curve can be established linking the concentration of the molecules in the liquid sample to the corresponding measured value of $T(\lambda_S)$ or $A(\lambda_S)$. The Beer-Lambert law further states that when there is more than one type of absorbing molecules in the liquid sample, the measured combined transmittance $T_{total}(\lambda_S)$ or absorption $A_{total}(\lambda_S)$ contributed by all the molecules is the measured sum of their individually contributed transmittances or absorptions at $\lambda_S$.

As disclosed by Wong and Campbell in U.S. Pat. No. 9,726,601 (2017), in formulating the theory to control interference noise for detecting molecules in liquids using the NDIR technique, a dominant absorption band of the interfering molecules $M_J$ (one or more kinds) at $\lambda_J$ is carefully selected for use. The interfering molecules $M_J$ are assumed to have a minor absorption at $\lambda_S$, the signal channel, which is interfering with the absorption of sample molecules $M_G$ at $\lambda_S$ used in their concentration level detection. The choice of $\lambda_J$ must be carefully made to make sure that no absorption bands for these interfering molecules $M_J$ exist dominantly elsewhere including at $\lambda_R$, the wavelength for the Reference channel except weakly at $\lambda_S$, the signal channel.

In the example of absorption spectra shown in FIG. 1, the targeted molecules $M_G$ have an absorption band at $\lambda_S = 1,150$ nm ($\lambda_S$) and the interfering molecules $M_J$ ($M_{J1}$ and $M_{J2}$) have an absorption bands at $\lambda_J = 1,210$ nm ($\lambda_J$). The interference bands $M_J$ also spectrally overlap the absorption band of targeted molecules $M_G$ at $\lambda_S$. In such a situation, the interference molecules $M_{J1}$ and $M_{J2}$, depending upon their concentrations, will generate Absorption Interference Noise (AIN) impacting the transmittance measurement of targeted molecules $M_G$ at $\lambda_S$. When a transmittance measurement of the liquid sample is made at $\lambda_S$, two parts are generated as a result of the application of Beer-Lambert Law as follows:

$$T_S(\lambda_S) = T_G(\lambda_S) + T_J(\lambda_S) \quad (2)$$

$$\text{and } T_J(\lambda_S) = \beta \times T_J(\lambda_J) \quad (3)$$

where $T_G(\lambda_S)$ is the transmittance of targeted molecules $M_G$ measured at $\lambda_S$, $T_S(\lambda_S)$ and $T_J(\lambda_J)$ are respectively the transmittances of the liquid sample measured at $\lambda_S$ and $\lambda_J$ and "$\beta$" in Equation (3) is a parameter indicating the ratio of the absorption strength of the interfering molecules measured respectively at wavelengths $\lambda_S$ and $\lambda_J$, namely, $$\beta = T_J(\lambda_S)/T_J(\lambda_J) \quad (4)$$

Rewriting Equation (2) for $T_G(\lambda_S)$ using Equations (3) and (4), one has $$T_G(\lambda_S) = T_S(\lambda_S) - \beta \times T_J(\lambda_J) \quad (5)$$

In Equation (5), both $T_S(\lambda_S)$ and $T_J(\lambda_J)$ are measured transmittances of the liquid sample respectively at wavelengths $\lambda_S$ and $\lambda_J$ except for "$\beta$" which is a constant parameter whose value changes only when the ratio of the absorption strength of the interfering molecules $M_J$ changes at $\lambda_S$ and $\lambda_J$. The value of "$\beta$" is independent of the concentration of the interfering molecules $M_J$. As long as the measured value of $T_J(\lambda_J)$ stays unchanged over time, so will $T_J(\lambda_S)$ since "$\beta$" is a constant. However, if $T_J(\lambda_S)$ stays unchanged, that means that the value of $T_G(\lambda_S)$, which determines the concentration of the targeted molecules $M_G$ in the liquid sample, will not be interfered by the presence of $M_J$. The earlier selected $\beta$-characterized calibration curve will stay valid (see later for more detailed explanation). But if $T_J(\lambda_J)$ changes over time due to the increase or decrease of the concentration of the interfering molecules, so will $T_J(\lambda_S)$ since the value of $\beta$ remains unchanged. Under this situation the value of $T_G(\lambda_S)$ in Equation (5) will change causing inaccuracy and invalidity of the $\beta$-characterized calibration.

Figure 3:
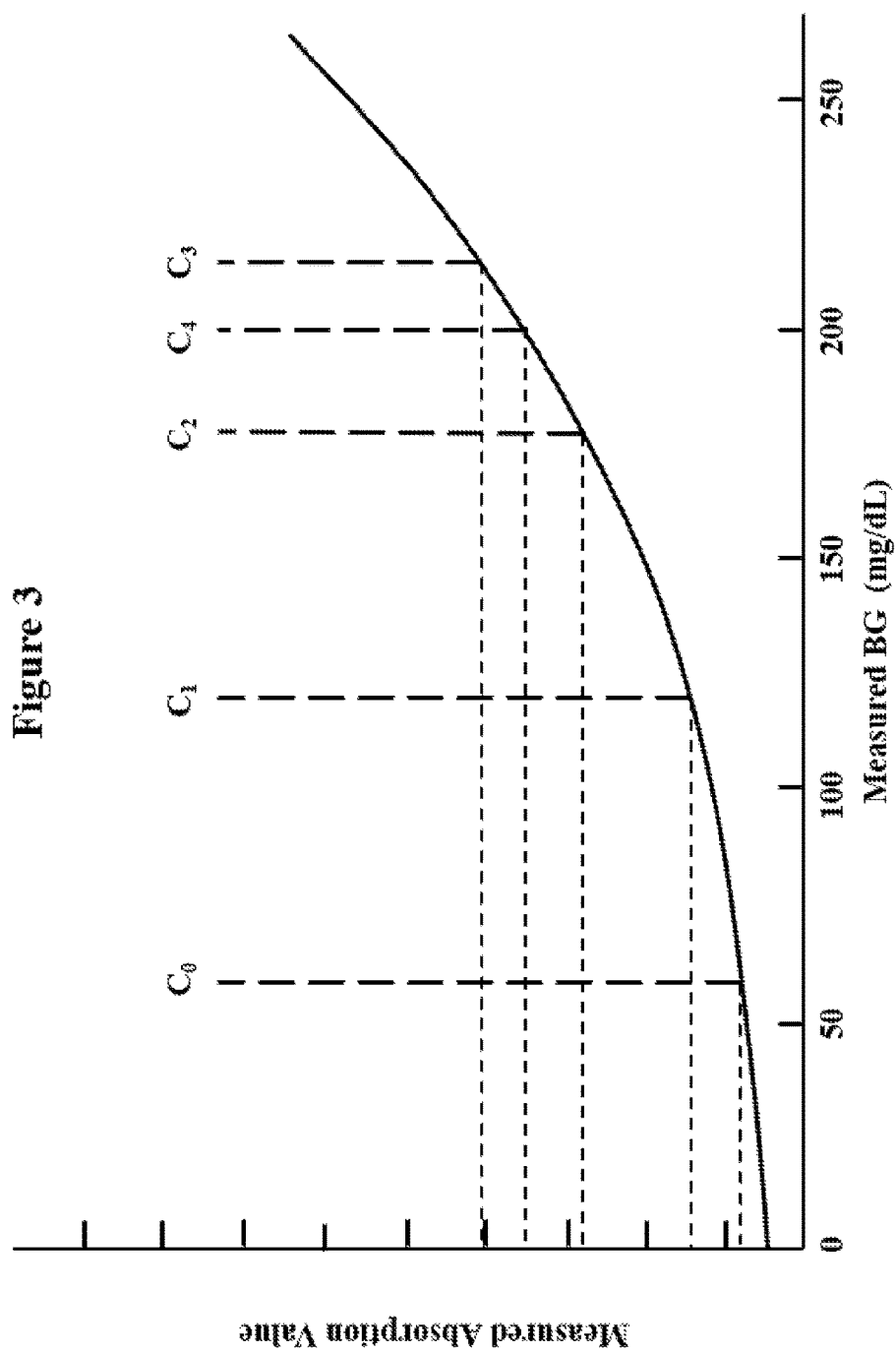
FIG. 3 shows implementation of the optimum Master Glucose Calibration Curve.

In order to implement the self-correcting technique, we assume the following:

1) A transmissive or reflected measured glucose value is comprised of two components: one is the actual glucose content in the sample $\lambda_S$ and one is the interfering component content that we call $\lambda_J$.
2) $\beta$ represents only a small contribution to the total absorption measurement.
3) This methodology arbitrarily assigns the value range of 0.05 to 0.25 to estimate changes in the overall $M_J$ interference effect.
4) Implementation of the optimum Master Glucose Calibration Curve FIG. 3 depends on incorporation of absorption effects by $M_J$ and is accomplished with the use of the appropriate $\beta$ value.
5) The Master Glucose Calibration Curve is that established in working with a clinician or doctor who monitors a dosing regimen to establish the relationship for an individual's optical transmission value matched to a "same time" blood glucose measured value.

Figure 2:
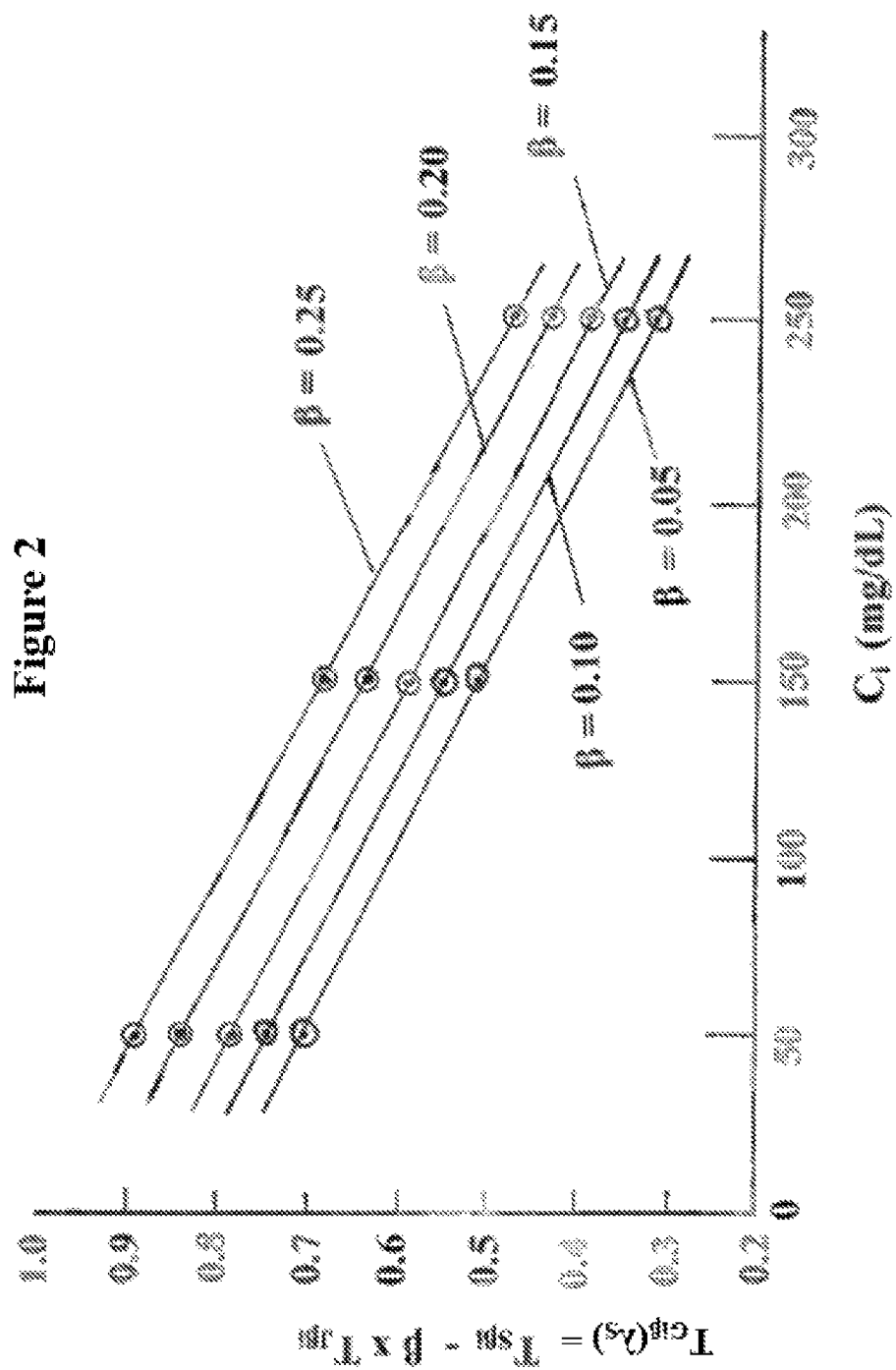
FIG. 2 shows the set of calibration curves $F(C_M, \beta)$ for concentration of molecules M in a liquid sample as a function of the absorption coefficient in the absence of Absorption Interference Noise (AIN) caused by interference molecules.

Let $V_{Si}(\lambda_S)$ and $V_{Ri}(\lambda_S)$ be the detector outputs (transmittances) at $\lambda_S$ for a set of concentrations $C_i$ of targeted molecules $M_G$ in the liquid sample and $T_{Si}(\lambda_S,t)=V_{Si}(\lambda_S,t)/V_{Ri}(\lambda_S,t)$ be the processed ratio at $\lambda_S$ for the signal and reference beams averaged over a time period "t". Let $V_{Si}(\lambda_J)$ and $V_{Ri}(\lambda_J)$ be the detector outputs (transmittances) at J for the same set of concentrations $C_i$ of targeted molecules $M_G$ in the liquid sample and $T_{Si}(\lambda_J,t)=V_{Si}(\lambda_J,t)/V_{Ri}(\lambda_J,t)$ be the processed ratio at $\lambda_J$ for the signal and reference beams averaged over a time period "t". Tabulate $\alpha=[T_{Si}(\lambda_S,t)-\beta \times T_{Si}(\lambda_J,t)]$ against concentrations $C_i$ of targeted molecules $M_G$ in the liquid sample with $\alpha$ as the ordinate and $C_i$ as the abscissa and obtain a family of five calibration curves with the value of $\beta=0.05$ to $\beta=0.25$ in $\beta$ increment value of 0.05 as shown in FIG. 2. Obtain also the average value of $T_{Si}(\lambda_J,t)=T_{Si}(\lambda_J,t)_{ave}=\gamma_0$ over all concentrations $C_i$ of targeted molecules $M_G$ in the liquid sample each measured over a time period of "t". The measurement operation is now complete with a set of five $\beta$-characterized calibration curves each with its own $\beta$ value (see FIG. 2) and a parameter $\gamma_0$ characterizing the average molecular environment of the interfering molecules $M_J$ surrounding the targeted molecules $M_G$ in the liquid sample during the calibration measurement.

In order to quantitatively calibrate the sensor for measuring the concentration of targeted molecules $M_G$ admixed with interfering molecules $M_J(M_{J1}$ and $M_{J2})$ in a liquid sample, four concentration standards $C_i$ ("i"=1 to 4) are employed. For each of the first three samples, namely $C_1$, $C_2$ and $C_3$, the transmittance value $T_{Gi\beta}(\lambda_S)=T_{Si}(\lambda_S)-\beta \times T_J(\lambda_J)$ is measured with $\beta=0.05$ to 0.25 with $\beta$ increment value of 0.05 as shown below:

$$C_1: T_{G1\beta}(\lambda_S)=T_{S1}(\lambda_S)-\beta \times T_J(\lambda_J); \beta=0.05, 0.10, 0.15, 0.20, 0.25 \quad (6)$$

$$C_2: T_{G2\beta}(\lambda_S)=T_{S2}(\lambda_S)-\beta \times T_J(\lambda_J); \beta=0.05, 0.10, 0.15, 0.20, 0.25 \quad (7)$$

$$C_3: T_{G3\beta}(\lambda_S)=T_{S3}(\lambda_S)-\beta \times T_J(\lambda_J); \beta=0.05, 0.10, 0.15, 0.20, 0.25 \quad (8)$$

and the average value of $T_{Si}(\lambda_J,t)_{ave}=\gamma_0$ for all three $C_i$ concentrations.

For each of the data curves shown in expressions (6), (7) and (8), there are three data points linking the glucose concentration $C_i$ (abscissa) with $T_{Gi\beta}(\lambda_S)$ [ordinate] for the five $\beta$ values (see FIG. 2). Expressions (6), (7) and (8) together represent five calibration curves linking $C_i$ (abscissa) to $T_{Gi\beta}(\lambda_S)$ [ordinate] at three $C_i$ values with the five different values of "$\beta$". Each of these five curves can be fitted to a simple binomial equation $C_i=F[T_{Gi\beta}(\lambda_S), \beta]$ for convenience of data analysis. Since "$\beta$" is an unknown quantity for each $C_i$ in the liquid sample under test, one simply does not know which of the five calibration curves is valid to be used. Therefore, in order to complete the calibration, one has to determine the correct $\beta$ value for the liquid sample under test and only the curve with that correct value of $\beta$ can be used as the calibration curve for $C_i$ in the liquid sample.

The correct value of "$\beta$" to be used is one of the set of five calibration curves as shown in FIG. 2 which can be determined with a fourth known concentration calibration sample $C_4$ when the other calibration standards, namely $C_1$, $C_2$ and $C_3$, are prepared. The first step is to capture the value of $T_{Gi\beta}(\lambda_S)$ and $T_{Si}(\lambda_J,t)$ and compare the value of $T_{Si}(\lambda_J,t)$ with that of the earlier stored value $T_{Si}(\lambda_J,t)_{ave}=\gamma_0$. If the difference is less than approximately 3%, which is very likely, since the molecular environment surrounding the targeted molecules $M_J$ has not changed much in this relatively a short time interval. The latest measured value of $T_{Si}(\lambda_J,t)$ will be stored in lieu of the earlier one for the next concentration measurement.

The next step is to use the captured value of $T_{Gi\beta}(\lambda_S)$ to determine which one of the set of calibration curves with different $\beta$ values as shown in FIG. 2 will give the value of $C_i$ closest to that of the known concentration calibration sample $C_4$ The $\beta$-characterized calibration curve in FIG. 2 that produces such a result would be the valid $\beta$-characterized calibration curve to be used for future measurements.

Figure 4:
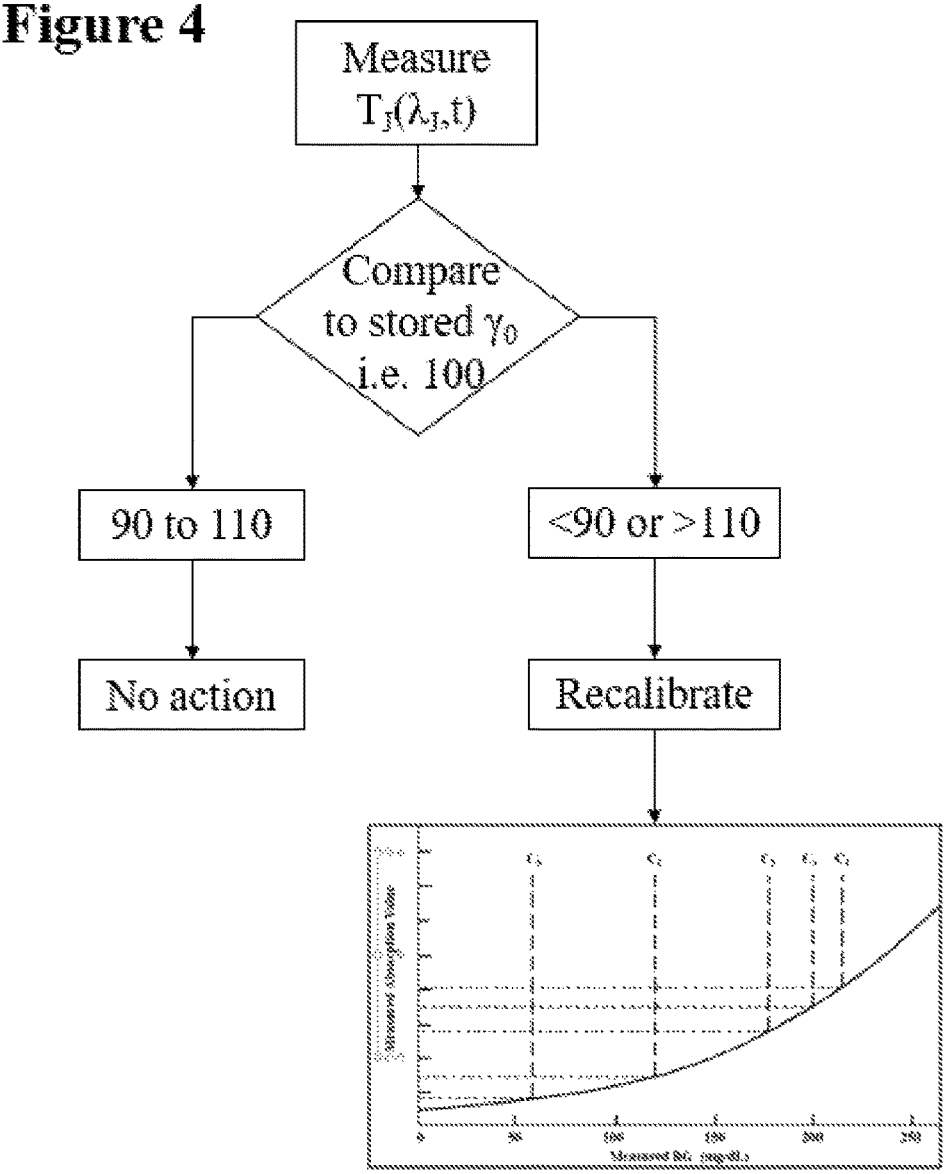
FIG. 4 shows the process flow for determining if a sensor recalibration is needed.

For subsequent measurement of $C_i$ ($C_i$ is the individual users concentration) using the monitor, one simply measures the values of $T_G(\lambda_S,t)$ and $T_J(\lambda_J,t)$). The first step is to compare the measured value of $T_J(\lambda_J,t)$ with the stored value $\gamma_0$. If there is a difference (+/−$\Delta$%), the measured value of $T_G(\lambda_S,t)$ has to be modified as $[T_G(\lambda_S,t)-\beta \times (1+/-\Delta\%) \times T_J(\lambda_J,t)]$ and then the stored $\beta$-characterized calibration curve is used to obtain the concentration of the targeted molecules $M_G$. If the difference $\Delta$ is approximately +/−10% or more, the monitor will need to be recalibrated before a follow-on set of measurements are captured. This process flow is described in FIG. 4.

An algorithm is implemented to compare the measured value of $T_J(\lambda_J,t)$ and the stored value, such that if this difference exceeds a certain level i.e. +/−10%, then that data from a requested recalibration will be captured, and an adjustment is made to shift the Master Glucose Calibration Curve to allow for the most current $T_J(\lambda_J,t)$ for utmost accuracy in measuring the target species glucose $M_G$.

Accordingly, it should be recognized that the present invention utilizes a calibration technique which goes further to establish a set of concentration curves for $\beta$ characterization for Rjavg(t2) while concentration standards are used to create the $\beta$ characterization calibration for the individual, calibration curves are fitted to an appropriately matching descriptive equation and a captured TGi$\beta$ ($\lambda$S) value is used to best choose a matching calibration curve for an individual non-invasive apparatus to enable the higher accuracy in sensing Ci.

While the invention described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternate embodiments without departing from the inventive concept.

What is claimed is:

1. A process for determining a concentration of a targeted molecule M within a given time period in a liquid sampling matrix in which at least one interfering molecule $M_J$ coexists with the targeted molecule by use of a non-invasive apparatus, comprising the steps of:

pulsing infrared radiation from a signal source, an interference source and a reference source into a multiplexer and collimating radiation leaving the multiplexer into a pulsed beam which is directed at a spot of the liquid sampling matrix;

detecting infrared radiation by a detector after it emerges from the spot as a pulsed signal and reference channel output and a pulsed interference signal and reference channel output from the pulsed beam after it penetrates into the spot;

using signal processing to obtain an average ratio value of $R_{ave}(t)$ for a first preselected period of time ("t") from the pulsed signal and reference channel output, where $R_{ave}(t)$=signal channel/reference channel output for the first preselected period of time;

using signal processing to obtain an average ratio value of $R_{Jave}(t_2)$ for a second preselected period of time ("$t_2$") from the pulsed interference and reference channel output, where $R_{Jave}(t_2)$=interference channel/reference channel output for the second preselected period of time;

determining a chosen calibration curve for the non-invasive apparatus;

using electronics to calculate the concentration of the targeted molecule M in the liquid sampling matrix by use of $R_{ave}(t)$ and the chosen calibration curve; and providing the concentration of the targeted molecule M in the liquid sampling matrix as an output from said electronics;

wherein the signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band;

wherein said at least one interfering molecule $M_J$ absorbs radiation at the signal wavelength;

wherein the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency; and wherein the chosen calibration curve is obtained by the steps of:

using the non-invasive apparatus to obtain a set of calibration curves for a set of different known concentration samples wherein each of the set of calibration curves contains a plurality of assumed β values, wherein β is a parameter indicating the ratio of the absorption strength of interfering molecules measured respectively at the signal wavelength and the interference wavelength;

using the non-invasive apparatus to calculate the concentration of the targeted molecule M in a known concentration calibration sample by use of $R_{ave}(t)$ and determining a best calibration curve of the set of calibration curves which achieves a calculated concentration closest to a known concentration of the known calibration sample; and using the best calibration curve as the chosen calibration curve.

2. The process of claim 1, wherein the pulsed beam is comprised of an alternate and sequential pulsing of a repeating pattern of the signal source, followed by the reference source, followed by the interference source, followed by the reference source.

3. The process of claim 1, wherein the pulsed beam is comprised of an alternate and sequential pulsing of a repeating pattern of the signal source, the reference source and the interference source.

4. The process of claim 1, wherein the frequency of N Hz is greater than 1.0 KHz with a duty factor of at least 10%.

5. The process of claim 1, wherein $t=t_2$.

6. The process of claim 1, wherein the signal beam has a signal beam center wavelength of 1,150 nm (1.150μ) and the reference beam has a center wavelength of 1,064 nm (1.064μ).

7. The process of claim 6, wherein the interference beam has a center wavelength of 1,210 nm.

8. The process of claim 7, wherein the targeted molecule M is glucose.

9. The process of claim 8, wherein said at least one interfering molecule $M_J$ is comprised of a plurality of interfering molecules contained in a body interstitial fluid.

10. The process of claim 1, wherein radiation emerging from the spot is collected by a lens onto the detector.

* * * * *